(12) United States Patent
Cho

(10) Patent No.: US 7,625,028 B2
(45) Date of Patent: Dec. 1, 2009

(54) FLIPPING DOUBLE HEADED TWEEZERS

(76) Inventor: Yong Hoon Cho, 604 Murfield Ct., Fullerton, CA (US) 92835

( * ) Notice: Subject to any disclaimer, the term of this patent is extended or adjusted under 35 U.S.C. 154(b) by 0 days.

(21) Appl. No.: 11/975,880

(22) Filed: Oct. 22, 2007

(65) Prior Publication Data
US 2009/0102215 A1 Apr. 23, 2009

(51) Int. Cl.
B25B 9/02 (2006.01)
(52) U.S. Cl. ...................... 294/99.2; 606/210
(58) Field of Classification Search ............ 294/3, 294/16, 99.2; 606/210, 211; 7/101, 118; D28/55
See application file for complete search history.

(56) References Cited

U.S. PATENT DOCUMENTS

| | | | | |
|---|---|---|---|---|
| 461,148 A * | 10/1891 | Fisher | ............ | 7/101 |
| 776,555 A * | 12/1904 | Settle | ............ | 269/6 |
| 2,334,252 A * | 11/1943 | MacGregor | ............ | 294/99.2 |
| 2,579,207 A * | 12/1951 | Scheib | ............ | 29/766 |
| 4,841,819 A * | 6/1989 | Williams | ............ | 81/3.8 |
| 5,449,374 A * | 9/1995 | Dunn et al. | ............ | 606/208 |
| 5,740,611 A * | 4/1998 | Schloss | ............ | 30/29.5 |
| D448,118 S * | 9/2001 | Grisoni | ............ | D28/55 |
| D456,076 S * | 4/2002 | Tyler | ............ | D24/143 |
| D521,685 S * | 5/2006 | Cho | ............ | D28/55 |
| 2008/0125810 A1* | 5/2008 | Cho | ............ | 606/211 |

* cited by examiner

*Primary Examiner*—Dean J Kramer
(74) *Attorney, Agent, or Firm*—Maria Erlinda Co Sarno

(57) ABSTRACT

A flipping double tweezers having a stationary and a movable tweezers. Each tweezers is formed from two elongated plates or molded as a single piece and has a tweezer head including a pincer and its tips and a fused rear section. The rear section of the stationary and the movable tweezers are designed to connect the tweezers and form a flipping mechanism whereby the movable tweezers can swing along a 180 degree orbit relative to the stationary tweezers.

20 Claims, 5 Drawing Sheets

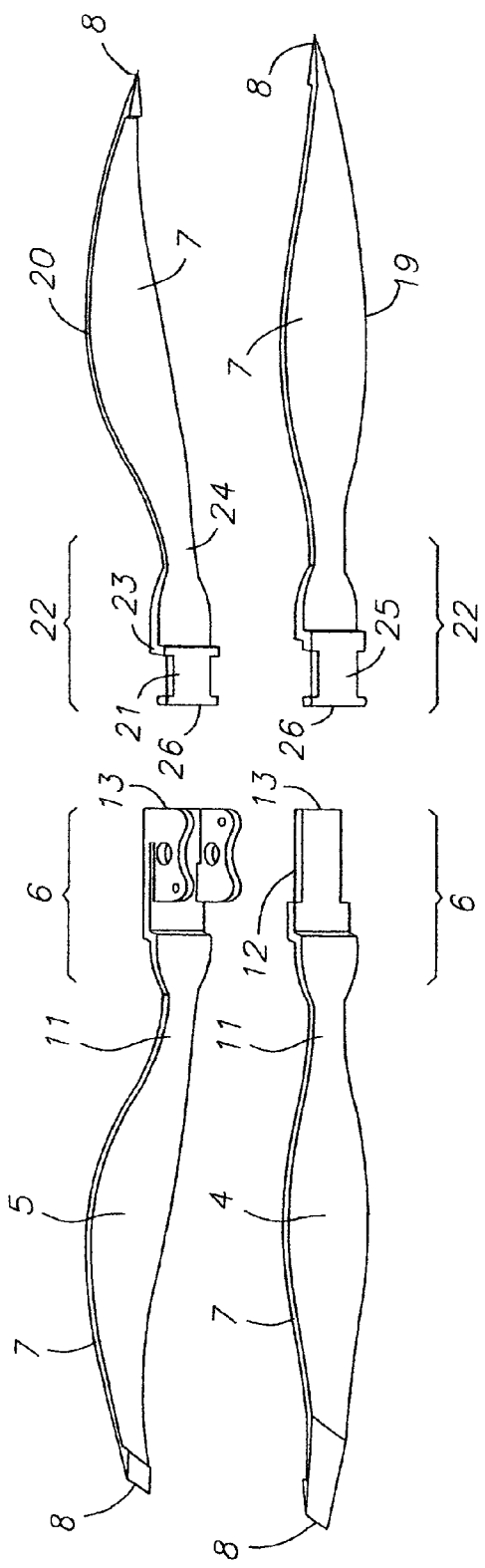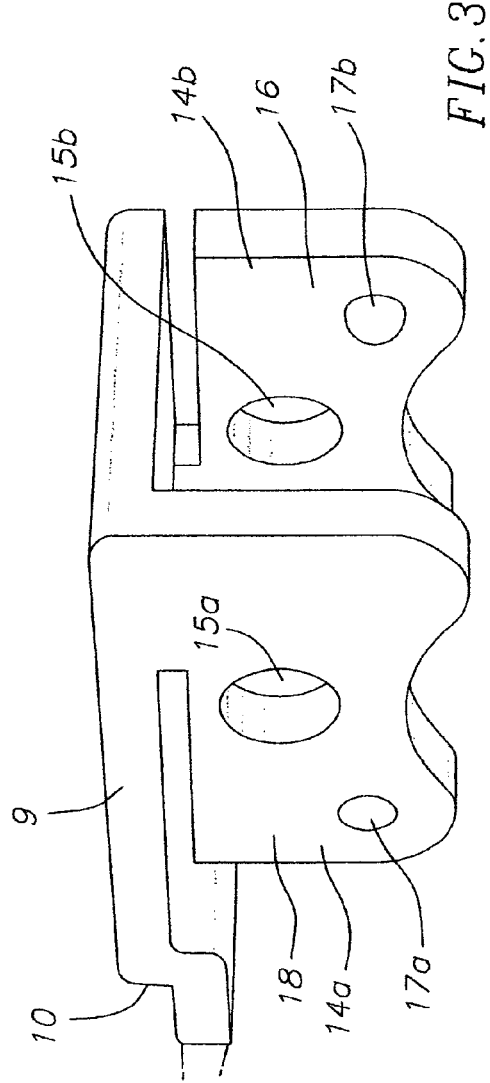

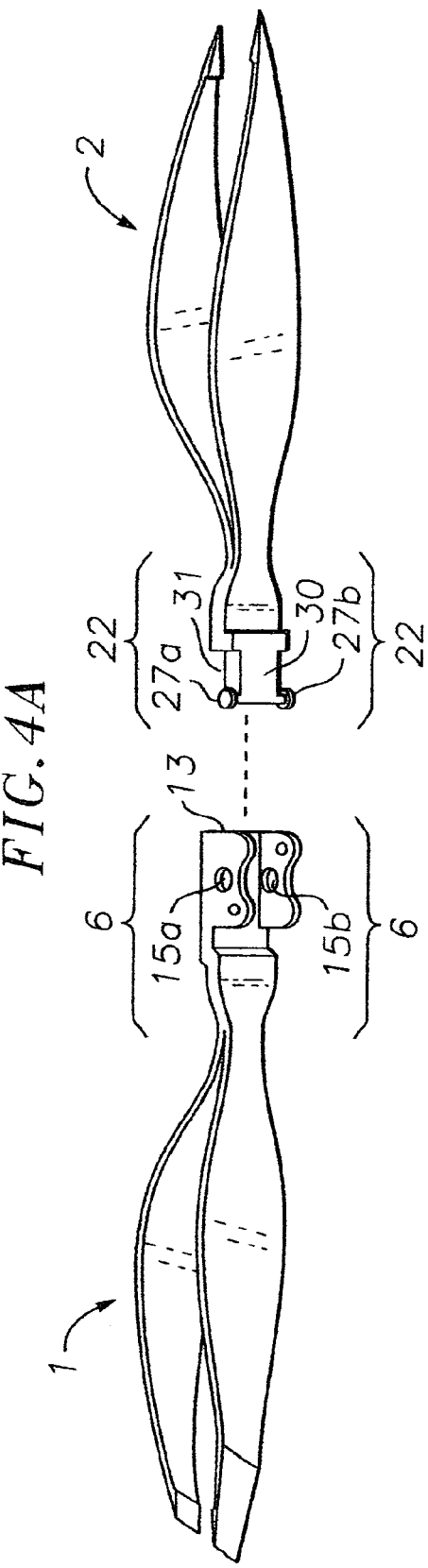
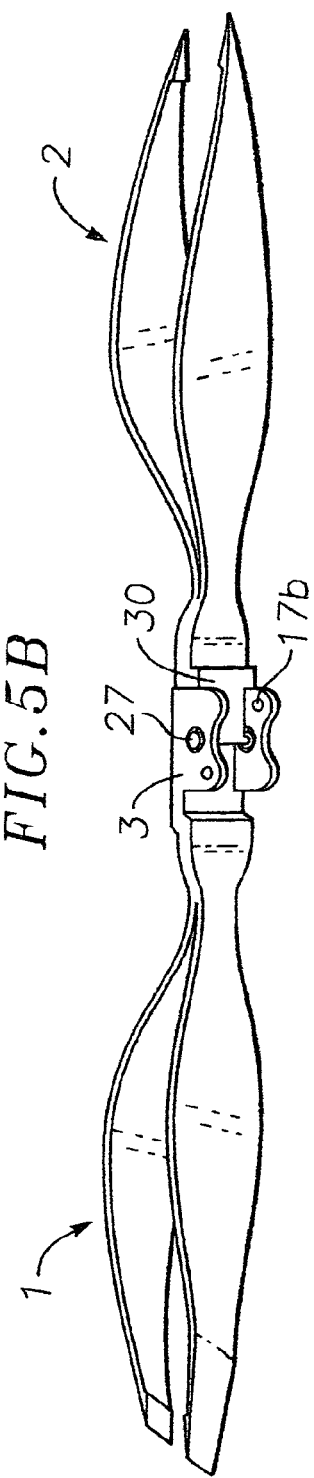

FLIPPING DOUBLE HEADED TWEEZERS

BACKGROUND

Current tweezers having two tweezer heads are constructed from two identical elongated thin flat sheets fused or joined together usually at a mid-position resulting in a pair of free moving opposing ends. The fusion at the center causes the opposite end to open up or space apart, consequently, allowing movement at this end as pressure by the fingers for example, is exerted or released at the outside surfaces of the elongated flat sheets proximal to the free moving end. The current tweezers, however, is straight and rigid. It does not allow one tweezer head to bend at an angle which may be desirable if two adjacent or closely situated objects are to be plucked or held at the same time or one after the other. Also, if the two tweezer heads or tweezers can be placed side by side, this would require a smaller space for storage as well as allow one cover to shield both tweezer heads to prevent the users and bystanders from getting hurt by its tips which are often sharp.

Having two tweezer heads instead of one in a single device is always desirable when multiple types of usage are desired. Different types or applications of tweezers are known. They are used in cosmetic, medical, dental, biochemical, microbiological, decorative, textile operations, to name a few. The shape of the tips of the tweezer heads vary and cater to the type of operation. Each tweezers herein may have a different head or the same head. Head in this application includes the pincer with its tips. The pincer as used here is the two free moving arms of the tweezers that picks or plucks an object. None of the known double headed tweezers have a flipping mechanism to enable one tweezer head to come side by side with the other head.

It is therefore an object of this invention to provide a device with more than one tweezer head to perform variable purposes or functions.

It is also an object of this invention to minimize the number of individual tweezers needed to carry on a desired function or operation.

It is a further object of this invention to provide a tweezers that have one tweezer head capable of flipping to lay side by side with the other tweezer head or swing at any angle relative to the other to be able to pluck or hold closely situated items at the same time or one after the other.

SUMMARY

The invention relates to a flipping double tweezers, comprising a first stationary tweezers and a second movable tweezers. Each tweezers having a tweezer head including a pincer and its tips and a fused rear section are formed from two elongated plates. The rear sections of the first and second tweezers are constructed to connect and form a flipping mechanism comprising an elevated flat section having two lateral side walls extending downwards with each side wall having a circular opening aligning with each other at the rear section of the first tweezers and a depressed flat section having protruding ends extending laterally at its rear edge situating below the elevated flat section of the first tweezers at the rear section of the second tweezers. The protruding ends of the second tweezers situate inside the circular opening of the first tweezers connecting the first tweezers with the second tweezers. The protruding ends rotate inside the circular opening as the second tweezers flip back and forth from a folding to an unfolding position relative to the first tweezers. To be able to rotate but stay within the opening, a rectangularly shaped protruding ends should have a height slightly smaller than the diameter of the circular opening, just enough to be able to rotate within the opening. Likewise, if the protruding ends are circular in shape, the diameter should be slightly smaller than the diameter of the circular opening. One plate of the two elongated plates forming each tweezers superimpose on the other plate and the rear section is fused together. There are known methods of joining or adhering two flat surfaces. Spot welding is one of them. The rear section of the tweezers extend from a rear section of the pincer to the rear edge of the tweezers. An inward protruding concave protrusion on an inside wall of the lateral side walls keep the flipping double tweezers in a position. There are at least two inward protruding concave protrusions, one on each inside wall of the lateral side walls. The concave protrusion is below a bottom surface of the second tweezers when the flipping double tweezers is in the unfolded position where the two tweezers locate opposite each other with each tweezer head facing the opposite direction but below a top surface of the second tweezers when the flipping double tweezers is in the folded position where the tweezers locate each other side by side with each tweezer head facing the same direction. The movable tweezers swing along a 180 degree orbit relative to the stationary tweezers. The device can have a cover to shield both tweezer heads. Each tweezers can be molded as a single piece. So long as the design and dimensions are kept, each can be connected by inserting the rear section of the second tweezers below the rear section of the first tweezers using the example described above and in the following detailed description.

Other embodiments of the present invention will become readily apparent to those skilled in the art from the following detailed description, wherein it shows and describes only certain embodiments of the invention by way of illustration. As will be realized, the invention is capable of other and different embodiments and its several details are capable of modification in various other respects, all without departing from the spirit and scope of the present invention. Accordingly, the drawings and detailed description are to be regarded as illustrative in nature and not as restrictive.

BRIEF DESCRIPTION OF THE DRAWINGS

Aspects of the present invention are illustrated by way of example, and not by way of limitation, in the accompanying drawings, wherein:

FIG. 2 shows the major parts of the flipping double tweezers prior to assembly of the device.

FIG. 3 is an enlarged view of the rear section of plate 5 of tweezers 1.

FIG. 4A is a perspective view of the two tweezers having molded rear sections.

FIG. 5B is a perspective view of the two tweezers joined together forming the flipping mechanism at the center having circular protruding ends on the depressed flat sections of one tweezers fitting into matching circular openings at the lateral side walls of the other tweezers.

DETAILED DESCRIPTION OF THE INVENTION

The detailed description represented herein is not intended to represent the only way or the only embodiment in which the claimed invention may be practiced. The description herein is provided merely as an example or examples or illustrations of the claimed invention and should not be construed as the only way or as preferred or advantageous over other embodiments or means of practicing the invention. Any tweezers with a multiple head that can flip or swing to and away from each other is within the scope of this invention. The detailed description includes specific details to provide a thorough understanding of the claimed invention and it is apparent to those skilled in the art that the claimed invention may be practiced without these specific details. In some instances, well known structures and devices may be shown in block diagrams or drawn with broken lines in order to either avoid obscuring the main concepts of the invention or to show the relationship of one part to the other.

Figure 1A:
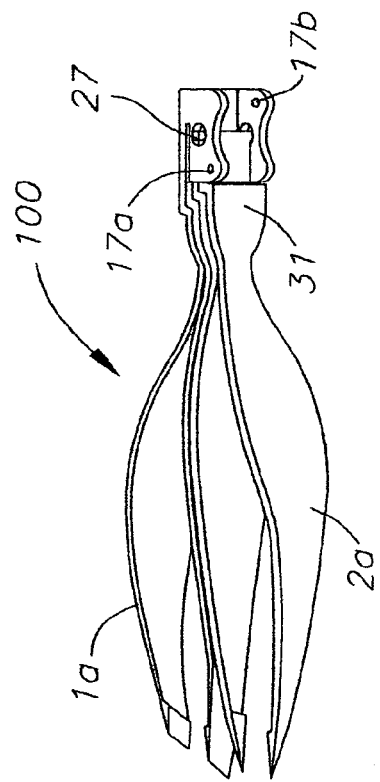
FIG. 1A is a perspective view of the flipping double tweezers with the two tweezer heads aligning side by side and facing the same direction.
Figure 1B:
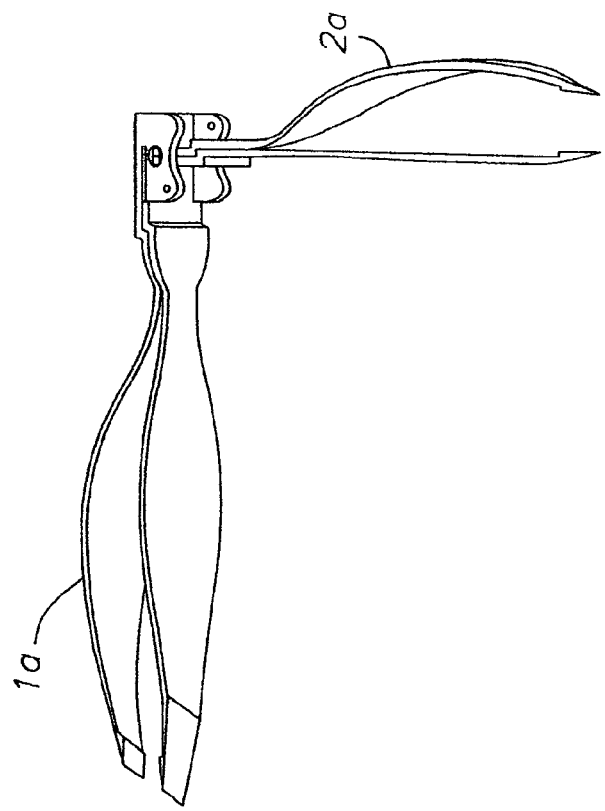
FIG. 1B is a perspective view of the flipping double tweezers with one tweezer head located perpendicular to the other tweezers.
Figure 5:
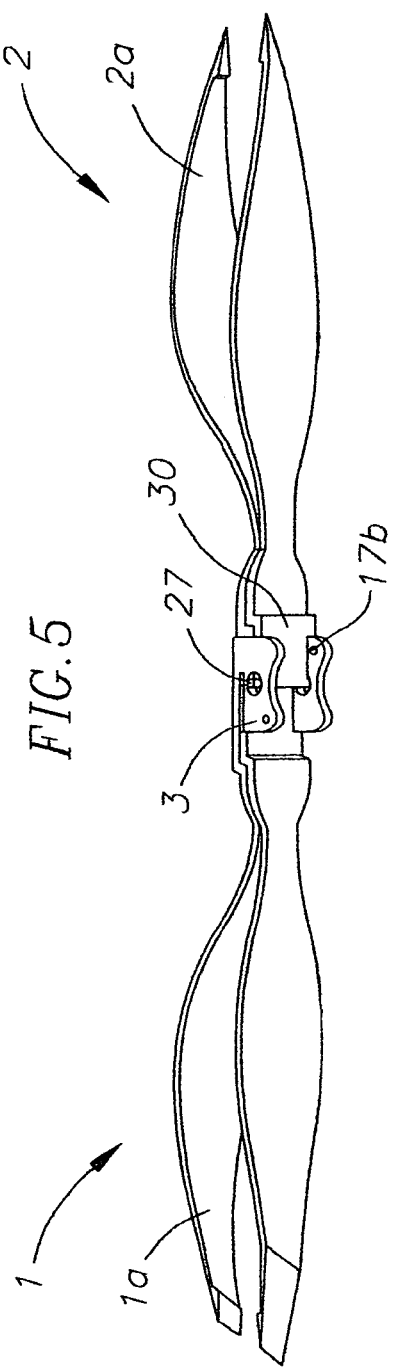
FIG. 5 is a perspective view of the two tweezers joined together forming the flipping mechanism at the center when the front end of the tweezers face in opposite direction.

The flipping double tweezers of this invention is shown in FIGS. 1A, 1B and 5. FIG. 1A shows the two tweezer heads 1a and 2a in a folded position, that is, located side by side with each other with the tweezer heads facing the same direction while FIG. 1B shows one tweezer head perpendicular to the other. FIG. 5 shows the two tweezers in an unfolded position with the tweezer head of the first tweezer facing a direction opposite the tweezer head of the second tweezers. FIGS. 1A, 1B and 5 show the main feature of this invention, the ability of one tweezers to swing along a 180 degree orbit in relation to the other.

Figure 1C:
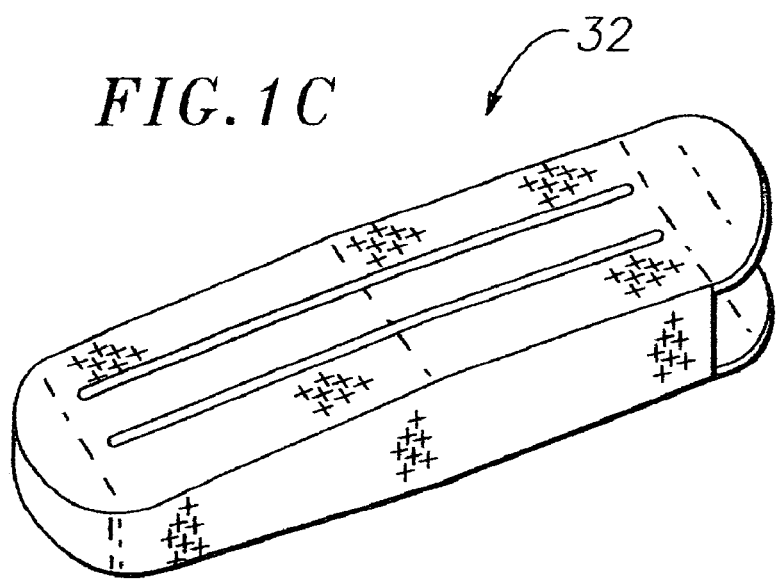
FIG. 1C and 1D are examples of covers that can be used for the flipping double tweezers shown in FIG. 1A.
Figure 1D:
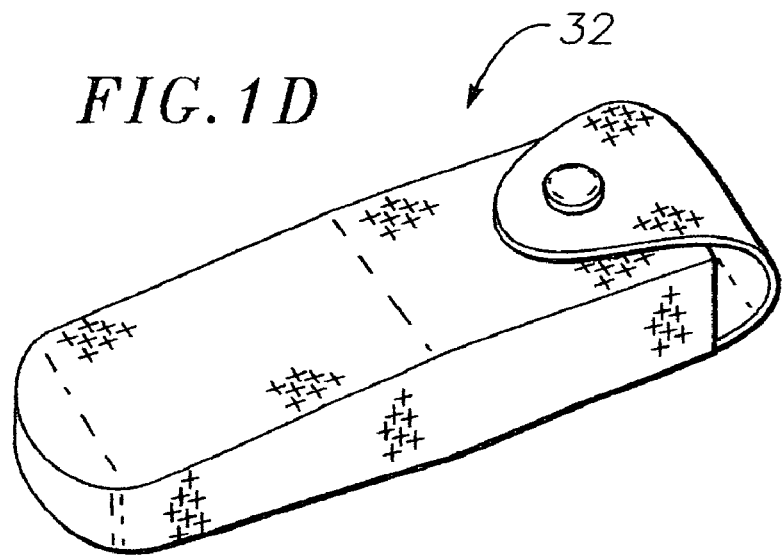

The flipping double tweezers 100 is made up of four major components or parts as shown in FIG. 2. The device herein is constructed from two separate tweezers, a first tweezers 1 and a second tweezers 2 instead of fusing two elongated flat sheets at a mid section to form two tweezer heads at opposite ends. The two separate tweezers are joined together by a flipping mechanism 3 which consequently makes the two tweezers, 1 and 2, appear like one device with two tweezer heads 1a and 2a. One tweezers 1 is made up of two elongated sheets or plates 4 and 5 joined or fused together at the rear section 6 to keep the front end free and movable. The front end includes the pincer 7 and its corresponding tips B which is also referred to as the tweezer head. The second tweezers 2 is also made up and constructed from the same basic parts. A cover 32 can be provided to shield both tweezer heads. Examples of covers that can be used to shield both tweezer heads are shown in FIGS. 1C and 1D. Herein, the same numerals will be used to identify the same parts on the two tweezers with the smaller letters used if further differentiation would assist in describing the device.

Figure 4:
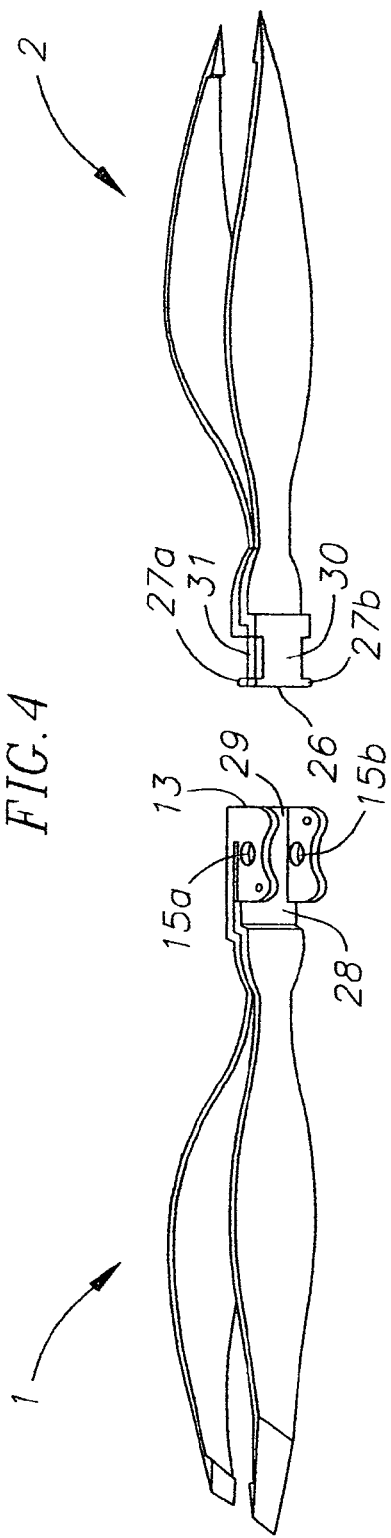
FIG. 4 is a perspective view of .the two tweezers after the fusion of the plates.

The two tweezers 1 and 2 differ in the design of their respective rear sections 6 and 22. Tweezer 1 will be described first. Tweezers 1 as shown in FIG. 2 is constructed from two elongated plates, 4 and 5 with one plate 5 superimposed on plate 4. Plate 5 extends to an elevated flat section 9 at the rear section 6 causing a step formation 10 proximal to the rear end 11 of the pincer 7 as shown in FIGS. 2, 3 and 4. Plate 4 also correspondingly extend to an elevated flat section 12. The rear section 6 extends from the rear end 11 of the pincer 7 to the rear edge 13 of the tweezers. The two plates are joined or fused together at the respective rear section 6 of plates 4 and 5 as shown in FIG. 4 by known methods such as gluing, spot welding and the like. Instead of joining two plates, tweezers 1 can also be molded as a single piece as shown in FIG. 4A. The rear section 6 of plate 5 is detailed in FIG. 3. As shown, there are two lateral side walls 14a and 14b extending downwards from the elevated flat section 9. A circular opening 15 is bored at a mid central section of each lateral side walls. The circular openings 15a and 15b represent the circular opening 15 at each lateral side walls align with each other. At the rear bottom section of the inside wall 16 of the lateral side wall 14b is a concave protrusion 17b. A similar protrusion 17a exists at the front bottom section of the inside wall 16. Both 17a and 17b protrudes inwards, consequently, 17a is shown as a dimple on the outside surface 18 of the lateral side wall 14a.

Tweezer 2 is constructed similarly as tweezer 1. As shown in FIG. 2, tweezer 2 is also constructed from two elongated plates, 19 and 20 with one plate 20 superimposed on plate 19. Plate 20 extends to a depressed flat section 21 at the rear section 22 causing a step formation 23 proximal to the rear end 24 of the pincer 7 as shown in FIG. 2. Plate 19 also correspondingly extend to a depressed flat section 25. The rear section 22 extends from the rear end 24 of the pincer 7 to the rear edge 26 of the tweezers. The two plates are joined or fused together at the respective rear section 22 of plates 19 and 20 as shown in FIG. 4 by the same method used in fusing or joining rear section 6. As with tweezer 1, instead of joining two plates, tweezers 2 can also be molded as a single piece as shown in FIG. 4A. The rear edge 26 of the depressed flat sections 21, 25 of tweezer 2 is extended laterally to form protruding ends 27a and 27b.

The two tweezers are joined together by inserting the rear edge 26 of tweezer 2 below the bottom outside wall 28 on the elevated flat section of rear section 6 of tweezer 1 and squeezing in, the protruding ends 27a and 27b into the matching circular openings 15a and 15b as shown in FIGS. 4 and 5, consequently placing the depressed flat section below the elevated flat section. Although the width of the depressed flat section 21 and 25 of tweezer 2 is slightly narrower than the width of the elevated flat section 9 and 12 at the rear section 6 of tweezer 1, a slight force is needed to place the protruding ends inside the circular openings because the rear edge 26 with the protruding ends 27a and 27b has a width larger than the width of the channel 29 bordered by the inside walls 16 of the lateral side walls 14a and 14b into which tweezer 2 inserts to. After insertion, the protruding ends 27 on tweezer 2 which have a diameter or height just slightly smaller than the diameter of the circular openings 15, sit inside the opening with the exposed side of the protruding ends aligning with the outside surface 18 of the lateral walls of tweezer 1. Although the protruding ends 27 are here shown as rectangularly shaped with rounded edges to conform with the curvature of the round opening, the protruding ends can also be oval, elliptical or designed to be likewise circular as the openings 15 but of a slightly smaller diameter than the openings 15 as shown in FIG. 5B. The height or diameter of the protruding ends should be just enough to rotate the protruding ends within the opening and make it stay within the opening. As shown here, it is tweezers 1 which has the circular opening 15 that is stationary while tweezers 2 with the protruding ends is the one movable. The protruding ends rotate inside the openings when tweezers 2 flip back and forth from a folding to an unfolding position relative to the stationary tweezers 1. The rectangularly shaped protruding ends illustrate this motion better by noting the vertical position of the protruding ends 27 when the two tweezers are in the folded position as shown in FIG. 1A and in the fully unfolded position as shown in FIG. 5 but are in the horizontal position when the tweezers are perpendicular from each other as shown in FIG. 1B. When the two tweezers are in the fully unfolded position, the tweezer head 1a is facing opposite that of tweezer head 2a. The concave protrusions 17a and 17b keep the tweezers 2 in the folded, unfolded and perpendicular position relative to tweezers 1. The width of the channel 29 is narrowed at the location of the concave protrusion because the protrusion protrudes inwards. When the two tweezers are unfolded, concave protrusion 17b is below the bottom surface of tweezers 2 and keeps tweezers 2 in that position because the bottom surface 30 of tweezers 2 sits on top of the concave protrusion 17b as shown in FIG. 5. To position tweezers 2 out of the unfolded position into a perpendicular position relative to tweezers 1, for example, a slight force is required to let the lateral sides of the depressed flat section of tweezers 2 pass the concave protrusion 17b because as stated above, the width of the channel 29 is narrower at the point where the concave protrusion is located. To fold the two tweezers side by side, the lateral sides of the depressed flat section of tweezers 2 should pass the other concave protrusion 17a and the tweezers are kept in this folded position with the top surface 31 of tweezers 2 now sitting on top of the concave protrusion 17a.

While the embodiments of the present invention have been described, it should be understood that various changes, adaptations, and modifications may be made therein without departing from the spirit of the invention and the scope of the claims.

I claim:

1. A flipping double tweezers, comprising:
a first stationary tweezers and a second movable tweezers, each tweezers having a tweezer head including a pincer and its tips and a rear section formed from two elongated plates, the rear section of the first and second tweezers connecting the tweezers and forming a flipping mechanism comprising an elevated flat section at the rear section of the first tweezers, the elevated flat section having two lateral side walls extending downwards from the elevated flat section, the two lateral side walls each having a circular opening aligning with each other, a depressed flat section at the rear section of the second tweezers situating below the elevated flat section of the first tweezers, the depressed flat section having a rear edge extending laterally forming protruding ends, the protruding ends of the second tweezers situating inside the circular opening of the first tweezers and rotating inside the circular opening as the second tweezers flip back and forth from a folding to an unfolding position relative to the first tweezers.

2. The flipping double tweezers of claim 1 wherein a rectangularly shaped protruding ends have a height slightly smaller than the diameter of the circular opening, just enough to rotate and stay within the opening.

3. The flipping double tweezers of claim 1 wherein a circular protruding ends have a diameter slightly smaller than the diameter of the circular opening, just enough to rotate and stay within the opening.

4. The flipping double tweezers of claim 1 wherein one plate of the two elongated plates forming each tweezers superimpose on the other plate.

5. The flipping double tweezers of claim 1 wherein the rear section is fused.

6. The flipping double tweezers of claim 1 wherein the rear section extends from a rear section of the pincer to the rear edge of the tweezers.

7. The flipping double tweezers of claim 1 further comprising an inward protruding concave protrusion on an inside wall of the lateral side walls to keep the flipping double tweezers in a position.

8. The flipping double tweezers of claim 7 wherein there are at least two inward protruding concave protrusions, one on an inside wall of each lateral side walls.

9. The flipping double tweezers of claim 7 wherein the concave protrusion is below a bottom surface of the second tweezers when the flipping double tweezers is in the unfolded position.

10. The flipping double tweezers of claim 7 wherein the concave protrusion is below a top surface of the second tweezers when the flipping double tweezers is in the folded position.

11. The flipping double tweezers of claim 1 wherein the movable tweezers swing along a 180 degree orbit relative to the stationary tweezers.

12. The flipping double tweezers of claim 1 wherein the two tweezers locate each other side by side in the folded position with each tweezer head facing the same direction.

13. The flipping double tweezers of claim 1 wherein the two tweezers locate opposite each other in the unfolded position with each tweezer head facing the opposite direction.

14. The flipping double tweezers of claim 1 further comprising a cover to shield both tweezer heads.

15. The flipping double tweezers of claim 1 wherein each tweezers is molded as a single piece.

16. A flipping double tweezers, comprising:
a first stationary tweezers and a second movable tweezers, each tweezers having a tweezer head including a pincer and its tips and a rear section formed from two elongated plates, the rear section of the first and second tweezers connecting the tweezers and forming a flipping mechanism comprising an elevated flat section at the rear section of the first tweezers, the elevated flat section having two lateral side walls extending downwards from the elevated flat section, the two lateral side walls each having a circular opening aligning with each other and an inward protruding concave protrusion on an inside wall of each lateral side walls, a depressed flat section at the rear section of the second tweezers situating below the elevated flat section of the first tweezers, the depressed flat section having a rear edge extending laterally forming protruding ends, the protruding ends of the second tweezers situating inside the circular opening of the first tweezers and rotating inside the circular opening as the second tweezers flip back and forth from a folding to an unfolding position relative to the first tweezers.

17. The flipping double tweezers of claim 16 wherein each tweezers is molded as a single piece instead of fusing two elongated plates.

18. The flipping double tweezers of claim 16 wherein the movable tweezers swing along a 180 degree orbit relative to the stationary tweezers.

19. The flipping double tweezers of claim 16 wherein the concave protrusion is below a bottom surface of the second tweezers when the flipping double tweezers is in the unfolded position.

20. The flipping double tweezers of claim 16 wherein the concave protrusion is below a top surface of the second tweezers when the flipping double tweezers is in the folded position.

* * * * *